(12) United States Patent
Diederichs

(10) Patent No.: US 9,248,542 B2
(45) Date of Patent: Feb. 2, 2016

(54) APPARATUS AND METHOD FOR PROCESSING A STENT

(75) Inventor: Christoph Diederichs, Ettlingen (DE)

(73) Assignee: ABBOTT LABORATORIES VASCULAR ENTERPRISES LIMITED, Dublin (IE)

( * ) Notice: Subject to any disclaimer, the term of this patent is extended or adjusted under 35 U.S.C. 154(b) by 1333 days.

(21) Appl. No.: 13/121,657

(22) PCT Filed: Sep. 29, 2009

(86) PCT No.: PCT/EP2009/007008
§ 371 (c)(1),
(2), (4) Date: May 31, 2011

(87) PCT Pub. No.: WO2010/037527
PCT Pub. Date: Apr. 8, 2010

(65) Prior Publication Data
US 2011/0221113 A1    Sep. 15, 2011

(30) Foreign Application Priority Data

Sep. 30, 2008    (EP) .................................... 08017219

(51) Int. Cl.
*B25B 5/06*    (2006.01)
*B23B 31/30*    (2006.01)
*B24B 33/02*    (2006.01)
(Continued)

(52) U.S. Cl.
CPC . *B24B 33/02* (2013.01); *A61F 2/91* (2013.01); *B23B 31/305* (2013.01); *B24B 37/02* (2013.01); *B25B 5/065* (2013.01); *Y10T 29/49998* (2015.01)

(58) Field of Classification Search
CPC . A61F 2240/001; A61F 2/91; Y10S 623/901; B23B 31/305; B23B 13/5016; B23B 5/065; B23B 31/003
USPC .............. 269/20; 427/2.24; 451/28, 238, 178, 451/180, 381, 541; 83/181; 76/37
See application file for complete search history.

(56) References Cited

U.S. PATENT DOCUMENTS 3,331,238 A * 7/1967 Kost ......................... F16J 10/02
                                                            73/49.5
3,516,681 A * 6/1970 Cox ....................... B23B 31/305
                                                            279/4.02
(Continued)

FOREIGN PATENT DOCUMENTS

DE         19628879       4/1999
WO    WO 2010037527       4/2010

*Primary Examiner* — Lee Wilson
*Assistant Examiner* — Jamal Daniel
(74) *Attorney, Agent, or Firm* — Workman Nydegger; John Kwok

(57) ABSTRACT

An apparatus for processing a medical stent that includes a holding device for holding a stent and a processing device for processing the stent held by the holding device that includes a first chamber for a fluid medium adapted to exert pressure around the stent. The first chamber for the fluid medium at least partially surrounds or encompasses the stent in the holding device that may include a housing which substantially encloses the first chamber for the fluid medium. A method of processing a medical stent is described. The method may include holding a stent with a holding device, and processing the stent with a processing device while holding the stent with the holding device. Holding the stent may include pressurizing a first chamber for a fluid medium to exert pressure around the stent. A method of producing or manufacturing a stent according to this method is described.

11 Claims, 4 Drawing Sheets

(51) Int. Cl.
 *A61F 2/91* (2013.01)
 *B24B 37/02* (2012.01)

(56) References Cited

U.S. PATENT DOCUMENTS

| | | | | |
|---|---|---|---|---|
| 3,542,354 A | * | 11/1970 | Fitzpatrick | 269/22 |
| 3,574,360 A | * | 4/1971 | Grawey | F16L 33/207 |
| | | | | 277/605 |
| 3,677,559 A | * | 7/1972 | Andre | B23B 31/305 |
| | | | | 279/4.03 |
| 3,751,050 A | * | 8/1973 | Hayes | B23B 31/305 |
| | | | | 269/22 |
| 4,714,289 A | * | 12/1987 | Arzenti | B23P 19/00 |
| | | | | 269/22 |
| 4,989,909 A | * | 2/1991 | Bouligny, Jr. | B25B 5/065 |
| | | | | 188/67 |
| 5,746,691 A | * | 5/1998 | Frantzen | A61F 2/91 |
| | | | | 451/36 |
| 6,086,455 A | * | 7/2000 | Frantzen | A61F 2/91 |
| | | | | 451/113 |
| 6,183,353 B1 | | 2/2001 | Frantzen | |
| 6,488,323 B1 | * | 12/2002 | Bouligny | B66C 1/46 |
| | | | | 269/22 |
| 6,537,202 B1 | * | 3/2003 | Frantzen | A61F 2/91 |
| | | | | 451/36 |
| 6,599,415 B1 | | 7/2003 | Ku et al. | |
| 7,658,880 B2 | * | 2/2010 | Wu | B29C 59/00 |
| | | | | 264/162 |
| 8,580,180 B2 | * | 11/2013 | Wu | B29C 71/02 |
| | | | | 264/162 |
| 8,733,408 B2 | * | 5/2014 | Pacetti | A61F 2/91 |
| | | | | 141/270 |
| 2008/0221664 A1 | | 9/2008 | Bales et al. | |
| 2008/0280025 A1 | * | 11/2008 | Scheer | 427/2.24 |
| 2014/0167324 A1 | * | 6/2014 | Wu | B29C 59/00 |
| | | | | 264/345 |

* cited by examiner

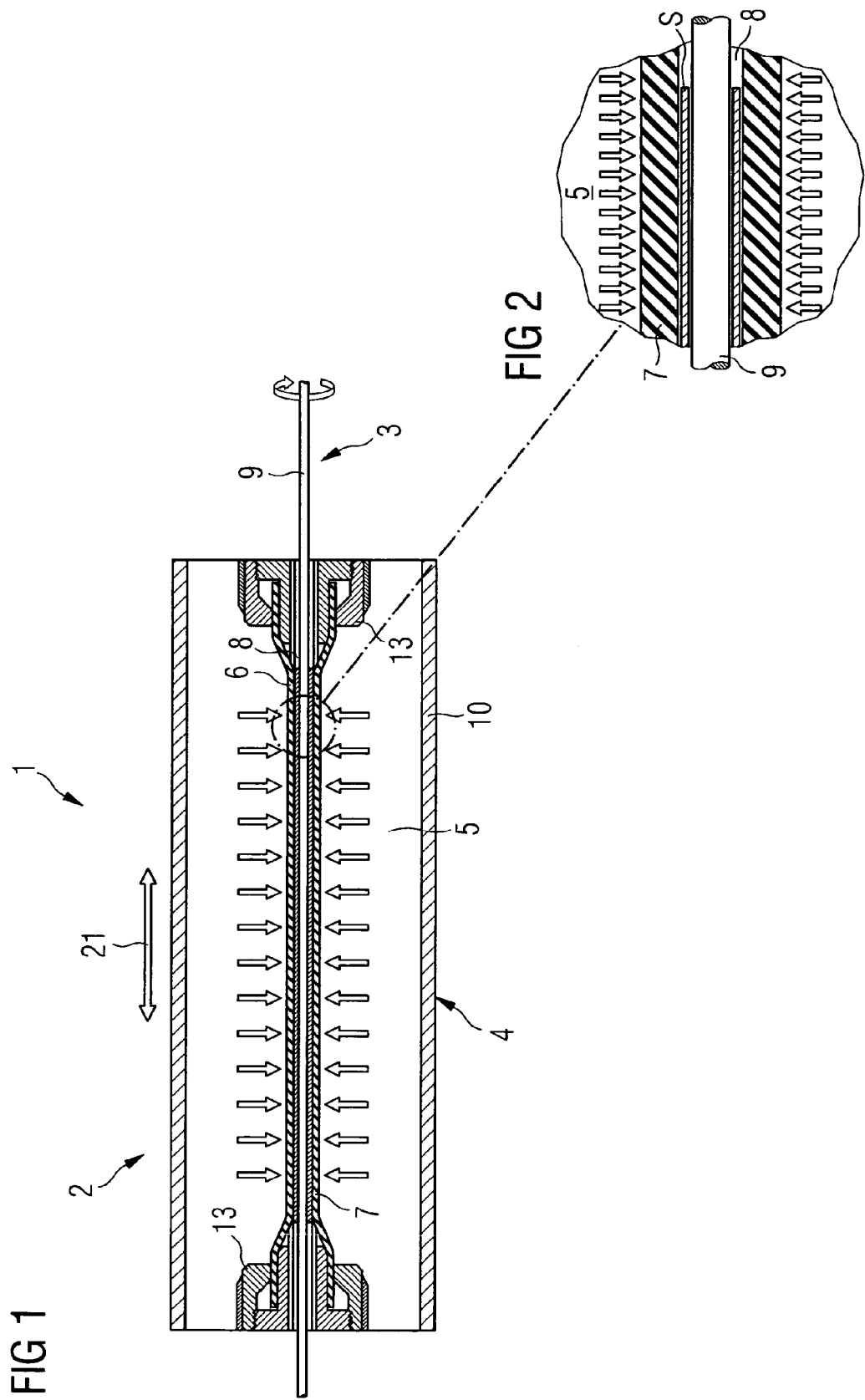

APPARATUS AND METHOD FOR PROCESSING A STENT

TECHNICAL FIELD

The present invention relates to an apparatus for processing a stent and, more particularly, to an apparatus for machining a stent; for example, an apparatus for machining internal surfaces of the stent. Furthermore, the invention relates to a method of processing a stent and, more particularly, to a method of machining a stent. In addition, the invention provides a stent which is produced or manufactured according to such a method.

BACKGROUND TO THE INVENTION

In the course of the past decade, the development and use of expandable stents in the medical field has grown enormously, to the point where stents today form a common element in the treatment of a wide variety of complaints and illnesses. Stents typically have a generally hollow cylindrical form and comprise a relatively intricate structure or framework of interconnected struts or arm members, which can be cut from a plain cylindrical blank. The cylindrical blank may be comprised of e.g. stainless steel, cobalt-chromium alloy, or nickel-titanium alloy (Nitinol).

Given the relatively fine and intricate nature of the stent structure, the stent framework is very often produced by laser cutting the cylindrical blank. While the laser cutting procedure is highly desirable in its ability to produce very small and yet very precise stent structures, it nevertheless has the disadvantage that it also generates residues of melted and re-solidified material (known as "slag") along the edges of the cut material. These slag residues produce rough or uneven deposits on the surfaces or edges of the stent struts or arm members, particularly on the inner surfaces and edges of the stent structure. The slag deposits and residues from the cutting procedure may normally be largely removed with a light scouring, scraping or abrading procedure. Nevertheless, even after such scraping, some remnants of the deposits remain, leaving burrs, cracks, pitting and/or surface unevenness.

Furthermore, the cylindrical metal blanks (e.g. stainless steel, cobalt-chromium alloy, or Nitinol) which are used to produce the stents are typically manufactured in a tube drawing process. This drawing process also typically generates roughening of the tube surfaces. The manufacturer of the tubular blanks will typically machine the outer surface of the tube material, e.g. by grinding, to a high level of smoothness before supplying the blanks for cutting into stents. The inner surfaces of the blanks, however, which later form the inner surfaces of the stent struts or arm members, are not ground prior to supply for stent production and therefore retain their roughness from the drawing procedure.

Importantly, it will be appreciated that burrs, pits, cracks, and other such surface imperfections can lead to stress concentrations and create weaknesses in the framework of the stent structure, thereby increasing the potential for failure of the stent. That is, such surface imperfections can lead to a localised overloading of the stent framework resulting in fracture, especially where multiple expansions of the stent occur, as is the case with Nitinol stents. Furthermore, pits, cracks and other such surface imperfections also serve as sites for the onset of corrosion, which may weaken the stent and potentially lead to failure of the stent in situ, i.e. in the patient. Accordingly, the removal of burrs, pits, cracks, and other such surface imperfections to provide very smooth stent surfaces is highly desirable for ensuring both fatigue resistance and corrosion resistance in use.

Although the insertion of a sleeve inside the cylindrical blank during the laser cutting procedure may be helpful to reduce splatter and slag formation on the stent, this technique does not completely eliminate slag formation and also has no bearing on the surface roughness created during formation of the blank by tube-drawing.

Thus, the use of an inner sleeve during laser cutting makes the cutting procedure more complicated and ultimately does not solve the problems of surface roughness.

A number of techniques have been employed to remove surface roughness from stents. One technique employed to smoothen stent surfaces is electro-polishing. Such a polishing technique, however, often proves ineffective for removal of excessive surface roughness because of the high rate of mass removal necessary. Chemical etching has also been employed to address the surface roughness and slag formation prior to electro-polishing. The chemical etching procedure, however, has the disadvantage that it removes material from all surfaces of the stent, even when the surface roughness to be treated is concentrated at the inner surfaces (e.g. on the internal diameter) of the stent structure. Furthermore, because pits and cracks in a surface are etched along with burrs and projections, chemical etching will not readily produce a plane surface. In addition, the chemical etching compound may not penetrate especially narrow or tight cracks and fissures, thereby potentially leaving regions of weakness in the stent surface. Thus, the use of chemical etching to smoothen the internal surfaces of the stent will generally remove more material than is necessary (e.g. from the external surfaces and side walls of the stent), will generally not produce a planar surface, and may not address all surface cracks and fissures.

Another technique for smoothing the surface roughness involves machining the inner surfaces of the stent to remove any remnants of slag and/or burrs and to eliminate pitting and cracks. In a conventional machining procedure the stent is held between parallel clamping elements or jaws and a file is inserted into the stent. This technique has the disadvantage, however, that the clamping elements or jaws tend to deform the stent and cause an uneven removal of material from the internal stent surfaces. Furthermore, the pressure from the clamping elements or jaws can cause the struts or arms of the stent framework to twist or bend during rotation of the file.

SUMMARY OF THE INVENTION

The present invention has been developed in light of the above disadvantages associated with conventional stent fabrication techniques. In particular, it is an object of the present invention to provide an apparatus and method for improved smoothening of internal stent surfaces and, in particular, for improved removal or reduction of burrs, pits, cracks, fissures and/or surface roughness.

The present invention provides an apparatus for processing a medical stent and a method of processing a medical stent as defined in the claims, as well as a stent produced according to such a method. Preferred features of the invention are recited in the dependent claims.

According to one aspect, therefore, the present invention provides an apparatus for processing a medical stent, comprising: a holding device for holding the stent, and a processing device for processing the stent held by the holding device, wherein the holding device comprises a first chamber for a fluid medium adapted to exert pressure on and/or around the stent. In a preferred form of the invention, the first chamber for the fluid medium at least partially surrounds or encompasses the stent when the stent is held by the holding device. More preferably, the first chamber for the fluid medium substantially fully surrounds or encompasses the stent in a circumferential direction when the stent is held by the holding device. The processing of the stent preferably involves machining, such as any one of grinding, filing, honing, or abrading of the stent surfaces, particularly the stent inner surfaces.

In a preferred form of the invention, the holding device comprises a housing which substantially encloses the first chamber for the fluid medium. The holding device preferably includes a second chamber or cavity for receiving the stent, with the first chamber for the fluid medium being separated from the second chamber or cavity by at least one wall which is moveable and/or flexible. This wall is preferably adapted to engage the stent when a fluid medium in the first chamber is pressurized. The stent may therefore be securely held within the second chamber or cavity under the action of the fluid pressure in the first chamber.

In a preferred form of the invention, the second chamber or cavity for receiving the stent is at least partially defined by the at least one moveable and/or flexible wall separating the first chamber from the second chamber. Accordingly, the first chamber for the fluid medium at least partially surrounds or encompasses the at least one moveable and/or flexible wall defining second chamber for receiving the stent, and preferably substantially wholly surrounds or encompasses the second chamber in a circumferential direction.

In a preferred form of the invention, the second chamber or cavity for receiving the stent has a substantially tubular or cylindrical form, which in turn is defined by a cylindrical or tubular movable and/or flexible wall. The wall is preferably formed from a flexible membrane, which is adapted to move and/or deform to engage the outer surface regions of the stent in the second chamber or cavity when the fluid medium in the first chamber is pressurized. In this way, pressurization of the first chamber with the fluid medium is adapted to exert pressure on the stent via the movable/flexible wall that separates the first chamber from the stent in the second chamber or cavity.

The at least one flexible wall is desirably comprised of a synthetic material, and more preferably of an elastomeric material such as silicone, and may hermetically seal or isolate the second chamber from the first chamber. When the at least one wall separating the first chamber from the second chamber comprises a flexible tube or a flexible cylindrical membrane which substantially surrounds or encircles the stent, the pressure applied in the first chamber thus causes the flexible tube or membrane to engage and press against the outer periphery and possible also the ends of the stent, whereby the pressure exerted on the stent is substantially uniformly distributed around the stent.

In a preferred form of the invention, the processing device comprises a machining device for machining (e.g. honing) the stent held by the holding device, with the machining device preferably including a machining tool, such as a honing mandrel. The machining tool is preferably axially insertable into the stent when the stent is held by the holding device. In other words, the machining tool is preferably insertable along a central or longitudinal axis of the stent.

In a preferred form of the invention, the machining tool is rotatable about an axis of rotation. The tool is preferably insertable into the stent along a direction of the axis of rotation. The machining tool may be elongate, with a longitudinal axis of the tool preferably extending substantially parallel to a central or longitudinal axis of the stent, and the longitudinal axis of the tool may correspond to the axis of rotation.

In a preferred form of the invention, the processing means (e.g. the machining tool) is adapted for reciprocating movement relative to the stent held by the holding device. Alternatively, or in addition, the holding device may be adapted for reciprocating movement relative to the processing means (e.g. the machining tool).

According to another aspect, the present invention provides a method of processing a medical stent, comprising the steps of: holding a stent with a holding device, and processing the stent with a processing device while holding the stent with the holding device, wherein the step of holding the stent comprises pressurizing a first chamber for a fluid medium to exert pressure on and/or around the stent. In a preferred form of the invention, the first chamber for the fluid medium at least partially surrounds or encompasses the stent circumferentially when the stent is held by the holding device. Indeed, the first chamber may substantially fully surround or encircle the stent circumferentially when the stent is held by the holding device.

In a preferred form of the invention, the step of pressurizing the first chamber exerts pressure around the stent via at least one movable and/or flexible wall separating the first chamber from the stent. In this connection, the step of holding the stent preferably comprises receiving the stent in a second chamber, wherein the second chamber is at least partially defined by the at least one movable and/or flexible wall.

In a preferred form of the invention, the step of processing the stent comprises inserting a processing tool into the stent when the stent is held by the holding device. In a particularly preferred form of the invention, the step of processing the stent comprises machining the stent with a machining tool, for example, by any one of grinding, filing, honing, or abrading.

In a preferred form of the invention, the step of machining the stent includes applying an abrasive medium to the machining tool. The abrasive medium may be in the form of a liquid or a paste containing an abrasive substance, e.g. abrasive particles. For example, the abrasive medium may comprise a diamond paste or a similar substance. The machining tool itself may be a plain mandrel devoid of any appreciable abrading profile, such that the abrasive medium applied thereto is essentially wholly responsible for the machining work, naturally in conjunction with the movement (e.g. rotation) of the tool relative to the stent.

In a preferred form of the invention, the step of machining the stent may comprise inserting the machining tool axially into the stent. Preferably, the step of machining the stent comprises rotating the machining tool about an axis of rotation, the axis of rotation preferably being substantially parallel to a central axis of the stent.

In a preferred form of the invention, the step of processing the stent comprises reciprocally moving the stent held by the holding device relative to the machining tool. Alternatively, or in addition, the step of processing the stent may comprise reciprocally moving the machining tool relative to the stent held by the holding device.

The present invention has the substantial advantage that the holding device securely holds the stent by pressure which acts essentially uniformly around the stent. In other words, the at least one wall of flexible material separating the first chamber from the second chamber may engage the circumferential sides of the stent as well as the axial ends of the stent when the fluid medium in the first chamber is pressurized. Thus, not only is the pressure distributed uniformly around the stent, but the force applied to the stent can be regulated to a very high degree by adjusting the pressure in the first chamber. In this regard, by incorporating an over-pressure valve, a relief valve or a similar mechanism in the holding device (e.g. in the housing), an inadvertent or unintended over-pressurization of the first chamber can be avoided.

The application of a highly regulated and uniform pressure around the stent overcomes the problems known from prior art machining devices. That is, an even or uniform removal of material from the inner surfaces of the stent can be achieved, and the stent framework does not tend to twist or bend. Furthermore, as material is initially removed from the inner surfaces of the stent structure during machining, the pressure in the first chamber can be increased to slightly compress the stent and thereby increase the interaction between the machining tool and the inner surface of the stent. This may continue until the desired amount of material has been removed and the desired level of surface smoothness has been obtained.

The present invention also has the advantage that, by application of a negative pressure in the first chamber, the flexible wall separating the first chamber from the stent can be drawn away from the stent to thereby release the stent from the holding device. In a preferred form, therefore, the method of the invention further comprises the step of de-pressurizing the first chamber and/or applying a negative pressure (e.g. partial vacuum) to the first chamber to remove the pressure acting on and/or around the stent. This thereby serves to release the stent from the holding device.

Stents produced according to the method of the present invention therefore have a significantly more uniform wall-thickness and a significantly improved surface smoothness at the inner surfaces of the stent. The strut thicknesses may remain essentially unchanged from the thicknesses as cut by the laser cutting procedure by avoiding the need for chemical etching. This leads to a more precise dimensioning of the stent structure and also produces planar inner stent surfaces.

Accordingly, the present invention enables a more preferential removal of material from the stent, and in particular from the internal surfaces of the struts or arm members of the stent framework, compared to the prior art techniques. This provides much greater design freedom and better control over the final dimensions of the struts. In particular, the present invention provides a production method for stents which reduces product variability and delivers the high tolerance required for specialised stent designs. The invention may potentially eliminate the need for any chemical etching procedure and may also reduce the need for electro-polishing.

The present invention is highly advantageous with standard stent dimensions having a wall-thickness of around 200 μm and strut widths of about 120 μm. In addition, however, the method and apparatus of the invention have been found particularly advantageous with specialised stents having very fine strut widths of about 80 μm. The machining of such stents with conventional clamping tools has been found to be extremely difficult, with the stents found to experience twisting and deformation of the struts or complete failure of the stent framework. Thus, the present invention enables the production of specialised stents which were not practicable with the prior art techniques. That is, the invention is particularly suitable for stents having a very low profile design, which can now be produced with very tight tolerances to ensure that the desired profile is achieved, but not at the expense of radial force.

Stents produced according to the present invention may be made from any one of stainless steel, cobalt-chromium alloy, or nickel-titanium alloy (Nitinol). Thus, the stents according to the invention may be self-expanding (e.g. temperature-sensitive), or may be designed to be expanded using a balloon-catheter, as is known in the art.

According to a further aspect, the present invention provides the use of an abrasive medium, such as a liquid or a paste, for machining surfaces of a stent. In a preferred form, the invention provides the use of an elongate tool having an abrasive medium in the form of a liquid or a paste applied thereto or coated thereon for machining surfaces of a stent, and in particular, inner surfaces of the stent.

BRIEF DESCRIPTION OF THE DRAWINGS

The above and further features and advantages of the present invention will become more apparent from the following detailed description of particular embodiments of the invention with reference to the accompanying drawing figures, in which like components are designated with like reference characters, and in which:

FIG. 1 is a schematic sectional side view of an apparatus for machining a stent according to a preferred embodiment of the present invention;

FIG. 2 is an enlarged view illustrating detail of that portion of the apparatus shown circled in FIG. 1;

DETAILED DESCRIPTION OF THE PREFERRED EMBODIMENTS

Figure 3:
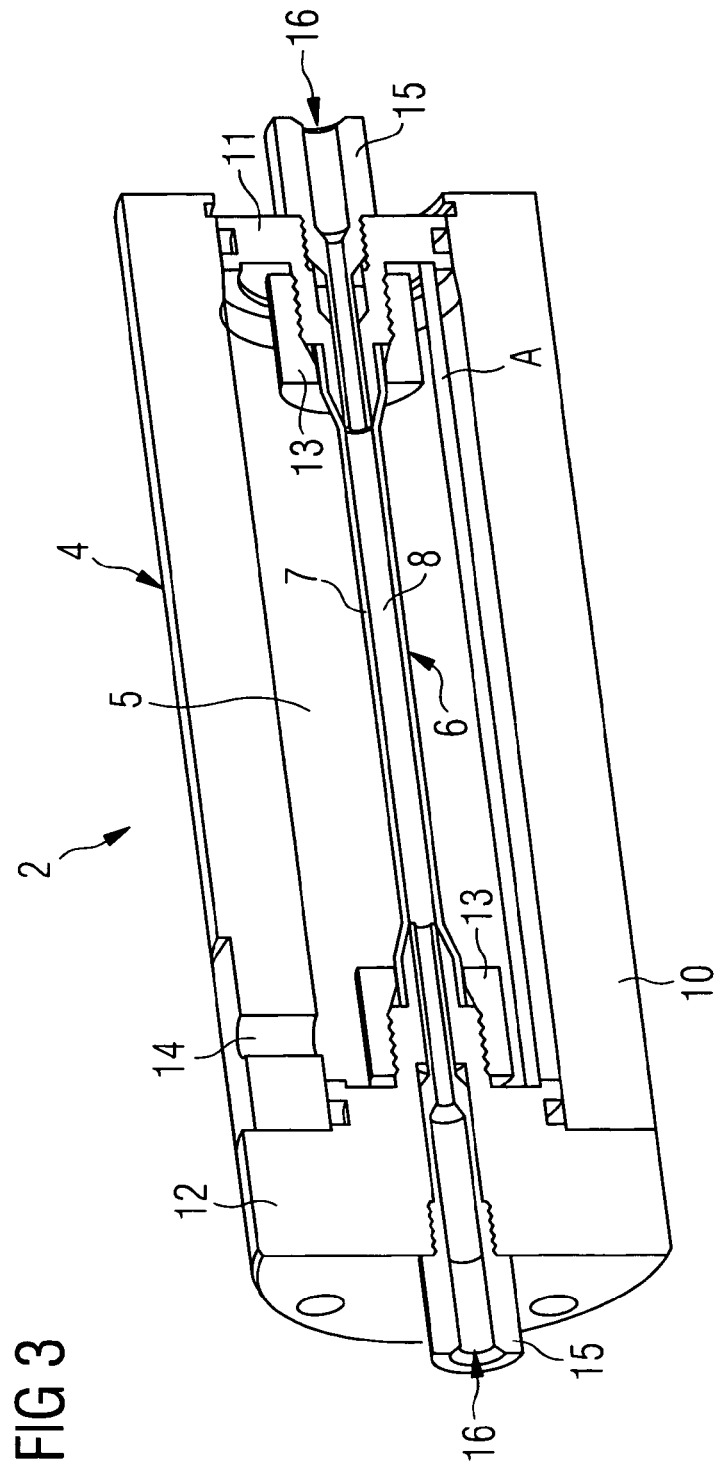
FIG. 3 is a schematic sectional perspective view of an apparatus for machining a stent according to an embodiment of the invention.

With reference firstly to FIG. 1 and FIG. 2 of the drawings, an apparatus 1 for machining a stent S according to an embodiment of the present invention is illustrated. The machining apparatus 1 comprises a holding device 2 for holding the stent S and a machining device 3 for machining one or more surfaces of the stent S. The holding device 2 comprises a housing 4 which substantially encloses a first chamber 5 which contains a fluid medium, such as a liquid. The liquid may conveniently be water, although any number of different liquids may be used. Equally, however, it will be appreciated that the fluid medium contained in the first chamber may also be a gas, such as for example air.

Centrally within the housing 4, a tubular member 6 formed of a flexible and resiliently deformable (e.g. elastic) material is provided. In the present example, this tubular member is formed from silicone. The wall 7 of the flexible tubular member 6 defines a second chamber 8 in the form of central cavity which is substantially surrounded or encompassed in a circumferential direction by the first chamber 5 accommodating the fluid medium. This second chamber 8 is adapted to receive the stent S to be machined, with the flexible tubular member 6 hermetically isolating or sealing the second chamber or cavity 8 from the liquid in the first chamber 5.

The machining device 3 comprises a machining tool 9 in the form of an elongate diamond file or honing mandrel, which is adapted for insertion into and through the second chamber or cavity 8 formed by the tubular member 6 in the holding device 2. This diamond file or honing mandrel is designed to rotate about its longitudinal axis such that it may machine, e.g. abrade, grind, file or hone, a metal surface with which it comes into contact during rotation. A liquid or pasty honing media, such as a diamond paste abrasive, is desirably applied to the machining tool 9 to facilitate the machining procedure. The grade or coarseness of the abrasive may be selected depending on the degree of surface machining required.

With reference now to FIG. 2 of the drawings, when the stent S is inserted into the cavity or second chamber 8 defined by the wall 7 of the flexible tubular member 6, and the rotatable machining tool 9 is inserted through the central longitudinal opening in the stent, the fluid medium (e.g. water) contained in the first chamber 5 enclosed within the housing 4 is pressurized. The pressurization of the fluid medium in the first chamber 5 may, for example, be effected by an operator using a small hand-pump device (not shown) or by connection to a fluid (e.g. gas) pressure source. Desirably, a pressure gauge is provided (in addition to any relief valve for preventing over-pressure) so that an operator can monitor the current pressure level in the first chamber 5. When the liquid in the first chamber 5 is pressurized to a predetermined level, the flexible wall 7 of the silicone tube member 6 defining the central cavity or second chamber 8 is moved and/or stretched under the force exerted by the fluid pressure into contact and firm engagement with the outside of the stent S received within the second chamber 8. This may naturally cause some small degree of circumferential and radial compression of the stent, depending upon the magnitude of the pressure generated.

The elongate machining tool 9 of the machining device 3 inserted into the stent S is then rotated by a rotary drive unit (not shown) to machine, hone, and smoothen the inner surfaces of the strut framework in the stent. As noted above, a filing and/or honing procedure may be improved by the application of a fluid (e.g. a liquid abrasive, such as diamond paste) onto the machining tool 9 before and/or during the machining procedure.

The pressure of the liquid in the first chamber 5 may be increased after an initial machining phase to force the inner surfaces of the stent structure into closer contact and engagement with the machining tool. The pressure in the first chamber 5 is distributed uniformly over the wall 7 of the silicone tubular member 6, as shown by the arrows in FIG. 1 and FIG. 2. Accordingly, the stent experiences a highly uniform application of the holding force around its circumference and at its ends, ensuring a secure and stable positioning of the stent within the holding device 2 during the machining operation. This, in turn, results in a highly uniform machining of the inner surfaces of the stent struts or arm members and avoids localized deformation of the struts, uneven removal of material, and/or failure of the stent structure when the struts or arm members have particularly thin dimensions.

Figure 4:
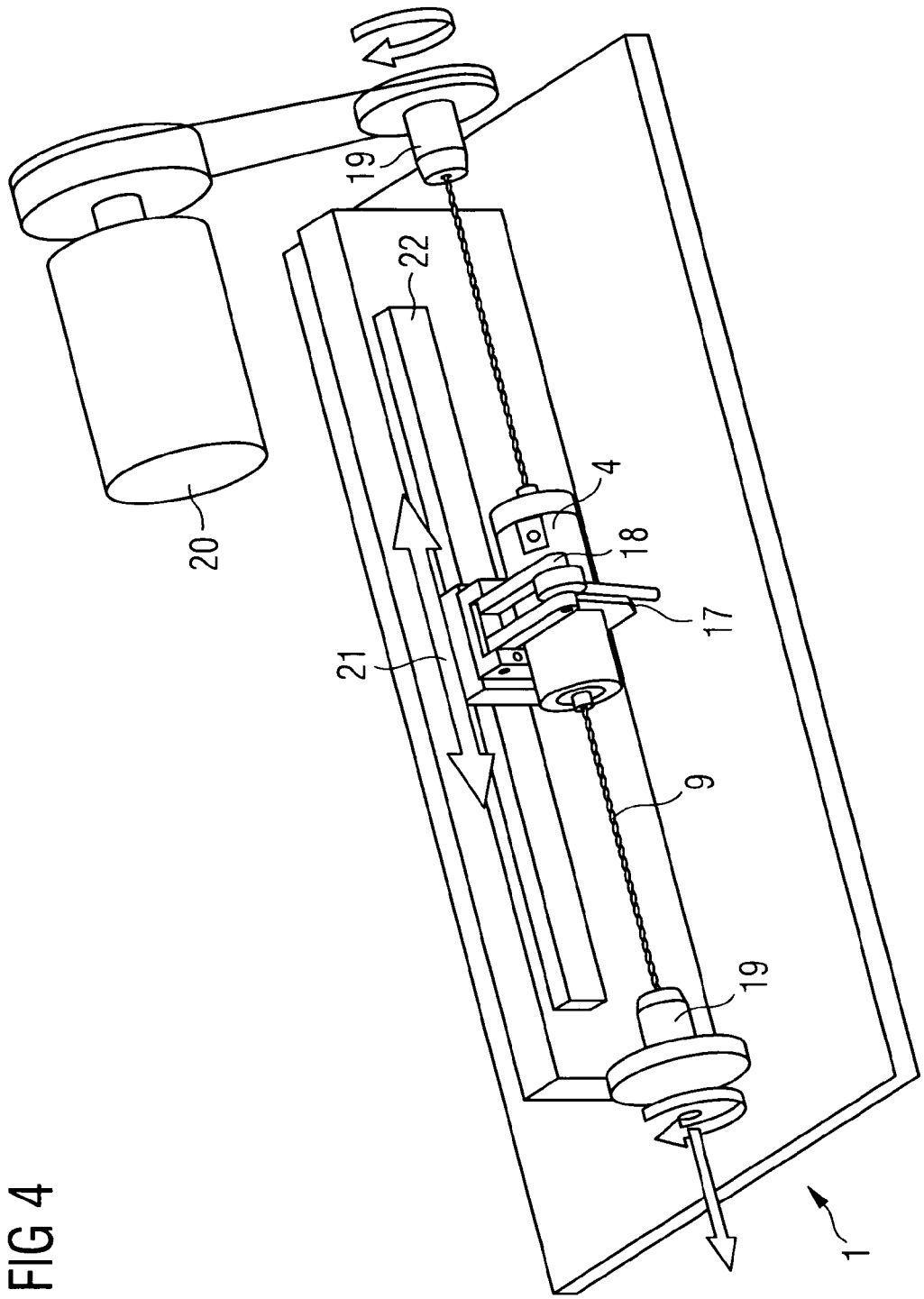
FIG. 4 is a schematic perspective view of an apparatus for machining a stent according to another preferred embodiment of the invention.

With reference now to FIG. 3 and FIG. 4 of the drawings, a more detailed example of a preferred embodiment of the machining apparatus 1 according to the present invention is illustrated. FIG. 3 of the drawings illustrates the general layout, again in cross-section, of the holding device 2 for holding the stent S during the machining procedure. In this embodiment, the holding device 2 again comprises a housing 4 having an outer, generally cylindrical casing 10 which, at one end, is closed by a plug member 11 mounted recessed within one end of the cylindrical casing and, at the other end, with a cap member 12 which covers that end of the casing 10.

As before, the casing 10 of the housing 4 encloses a first chamber 5 which has a generally annular form and circumferentially surrounds or encompasses a central tubular member 6 having a wall 7 made of a flexible and desirably also resiliently deformable (e.g. elastic) material, such as silicone. The ends of the tubular member 6 are respectively secured at the plug and cap members 11, 12 at opposite ends of the housing 4 by threaded collars or cap nuts 13 which are engaged with the plug and cap members 11, 12 in a manner as will be understood by a person skilled in the art. The collars 13 secure the opposite ends of the tubular member 6 such that the cavity or second chamber 8 enclosed by the flexible wall 7 of the tubular member 6 is hermetically sealed from the liquid in the first chamber 5.

At least one spacer member A is also provided in the housing 4 extending longitudinally within the first chamber 5 to ensure that the plug member 11 and the cap member 12 closing the ends of the casing 10 maintain a specific or predetermined distance from one another. A port 14 is formed through the casing 10 of the housing 4 to provide fluid communication with the first chamber 5. This port could be to fill or drain the fluid medium of the first chamber 5, as required. More typically, however, the casing 10 comprises two halves and these are assembled while submerged in the fluid medium (e.g. water) that is to fill the first chamber 5. This ensures the exclusion of bubbles. The port 14 is primarily used for pressurizing the fluid medium contained within the first chamber 5 by attaching a line or conduit to a pump device or pressure source (not shown).

Each of the plug member 11 and the cap member 12 of the casing 10 includes a tool guide member 15 having a central bore 16. The tool guide members 15 are threaded and screwed into respective apertures provided in the plug member 11 and the cap member 12 such that the central bores 16 of the guide members 15 are aligned and communicate with the second chamber 8 defined within the tubular member 6. The bores 16 are adapted to receive the elongate machining tool 9 and to guide same centrally through the second chamber or cavity 8 and through a stent S to be processed held in the second chamber. As shown in FIG. 4, the housing 4 of the holding device 2 is mounted within the machining apparatus 1 of the invention and an elongate machining tool 9 in the form of a diamond file or honing mandrel extends axially through the housing 4. The operation of the apparatus 1 according to the method of the present invention will now be described below.

Before the housing 4 of the holding device 2 is combined with the machining tool 9, a guide member 15 at one of the ends of the holding device casing 10 is removed (e.g. by unscrewing the guide member 15 from its position in threaded engagement within the plug member 11 or the cap member 12) and a stent S to be processed is inserted through the opening formed by removal of the guide member 15 into the second chamber 8 defined within the silicone tubular member 6. The fit is preferably relatively close or snug, but not tight, such that the flexible wall 7 of the tube 6 may lightly touch an outer surface of the stent S when the fluid medium within the first chamber 5 is not pressurized, but nevertheless allows the stent to be readily pushed into and along the tubular member 6 so as to be fully positioned within the second chamber 8. The guide member 15 is then replaced and screwed into its axially aligned position for receiving and guiding a machining tool 9 through the housing 4 of the holding device 2.

At this stage, it will be appreciated that a fluid medium is already present in the first chamber 5 and that, although removal of a guide member 15 from one end of the housing 4 provides access to the cavity or second chamber 8 defined by the flexible tubular member 6, the fluid medium contained in the first chamber 5 is hermetically isolated from the second chamber 8 by the silicone material of the flexible tube 6 and the screw collars 13 which seal the ends of the flexible tube 6 to the respective plug member 11 and cap member 12 at opposite ends of the casing 10.

Once the stent is positioned within the flexible tubular member 6, the housing 4 of the holding device 2 is mounted on a carriage 17 of the machining apparatus 1, as shown in FIG. 4. In particular, a hinged latching mechanism 18 on an upper side of the carriage 17 may be opened to allow insertion of the housing 4 into the carriage and then closed to secure the housing 4 in a fixed and stable position within the carriage. Next, an elongate machining tool 9 in the form of a cylindrical diamond file or honing mandrel is inserted and guided through one of the guide members 15 at an end of the housing 4, and in turn through the tubular member 6 along a central axis of the second chamber 8, and therefore also through a central opening of the stent S to be processed, which is positioned within the second chamber 8. In order to ensure that the insertion of the machining tool 9 does not inadvertently displace or push the stent along the length of the tubular member 6, the ends of the guide members 15 may function as stops to abut the ends of the stent. The machining tool 9 is then passed through the guide member 15 at the opposite end of the housing 4 and is received within a supporting chuck 19 outside of the housing. It will be noted that a diamond paste or machining liquid may be applied to the tool 9 prior to its insertion through the stent holding device 2 to facilitate the machining procedure.

With pressurization of the first chamber 5, the flexible wall 7 of the tube 6 moves to positively engage and hold the outer circumference of the stent, thereby ensuring a stable position for the stent during machining. The fluid pressure may also lightly compress the stent to ensure the desired proximity between the machining tool 9 with honing media and the inside of the stent. A rotary drive 20 is activated to rotate the mandrel and thereby commence the machining procedure (e.g. filing, grinding, honing) at the internal surfaces of the stent held in the second chamber 8. As will be appreciated from the arrows 21 illustrated in FIG. 4, the carriage 17 holding the housing 4 of the holding device 2 is mounted on a linear drive mechanism 22 for executing a reciprocating movement relative to the elongate machining tool 9. This reciprocating movement of the housing, and therefore also of the stent, aims to ensure an even distribution of the liquid or pasty honing media and uniformity of the machining over a longitudinal extent of the stent held by the holding device 2.

After an initial machining phase, the pressure within the first chamber 5 may be increased to force the stent into a closer contact with the machining tool. A further machining phase may then ensue to achieve the desired amount of material removal and surface finish at the interior surfaces of the stent. To release the stent after the machining operation is finished and rotation of the tool 9 has been stopped, the first chamber 5 is de-pressurized and/or a negative pressure (partial vacuum) is applied to the first chamber 5 to draw the wall 7 of the tubular member 6 away from the stent. This releases the compressive pressure on the stent. The tool 9 may then be carefully withdrawn from the housing 4 and, after removing one of the tool guides members 15, the stent can be recovered from within the second chamber 8.

Figure 5A:
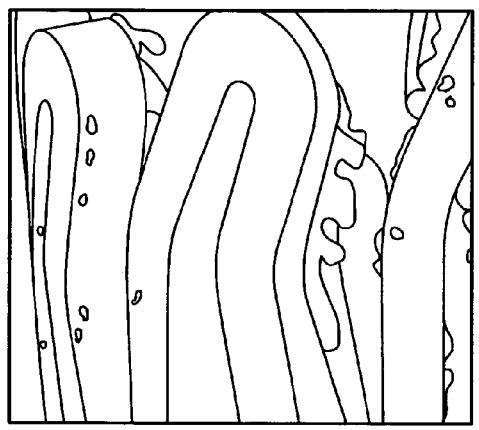
FIG. 5A is an image of an outer surface of a stent structure after laser cutting of the stent structure from a cylindrical blank.
Figure 5B:
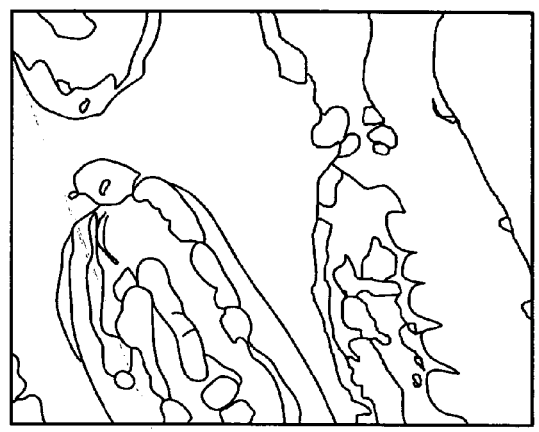
FIG. 5B is an image of an inner surface of a stent structure after laser cutting of the stent structure from a cylindrical blank.
Figure 6:
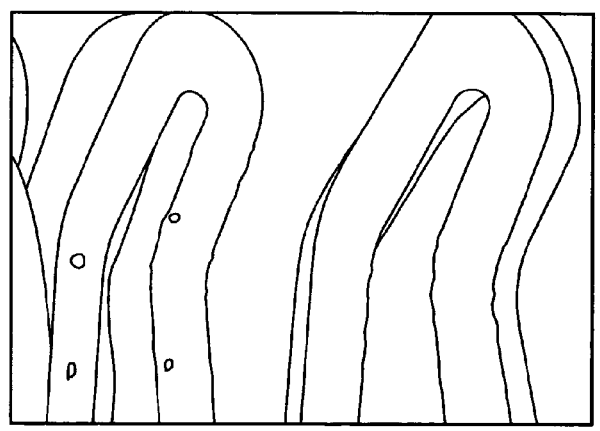
FIG. 6 is an image of an inner surface of a stent structure after processing with an apparatus and method according to a preferred embodiment of the present invention.

With reference now to FIGS. 5A and 5B of the drawings, a magnified view of part of the framework structure of a stent is shown after laser cutting of the stent structure from a cylindrical blank, but before processing the stent according to the present invention. The outer surfaces of the struts or arm members of the framework (particularly visible in FIG. 5A) are quite smooth whereas the inner surfaces of the struts (particularly visible in FIG. 5B) are rough and coated with slag residues from the cutting procedure. The slag deposits are removed to a large extent with an initial basic abrading process, then the inner surfaces of the stent are machined according to the method of the invention to produce the desired surface smoothness. FIG. 6 of the drawings shows a magnified view of the inner surfaces of the struts after processing the stent according to the invention.

It will be appreciated that the above discussion of particular embodiments of the invention with reference to the accompanying drawings is for illustrative purposes only. Accordingly, alterations and/or additions can be made to the particular parts of the embodiments described without departing from the scope of the invention defined in the following claims. For example, the holding device 2 of the apparatus may be modified to accommodate more than one stent at a time. That is, multiple stents could be inserted into the second chamber 8 of the holding device 2 (e.g. arranged spaced apart in a row) and processed simultaneously.

It will be appreciated, of course, that the apparatus 1 of the invention can also be adapted to different stent diameters and lengths by scaling the design as needed, e.g. by appropriate modification of the tubular member 6 and/or the guide members 15.

The invention claimed is:

1. An apparatus for processing a medical stent, comprising:
   a holding device for holding the stent, the holding device comprising a housing having a first end, a second end, a first chamber filled with a fluid medium, a second chamber located within the first chamber and defining a lumen extending from a first opening in the first end to a second opening in the second end for receiving the stent within the second chamber, and a flexible barrier separating the first chamber from the second chamber, wherein selective pressurization of the fluid medium causes the flexible barrier to contact an exterior surface of the stent and exert a substantially uniform pressure to substantially the entire exterior surface of the stent; and
   a machining tool for processing the interior surface of the stent held by the holding device, the machining tool extending the entire length of the lumen and beyond both ends of the housing.

2. The apparatus according to claim 1, wherein the first chamber for the fluid medium at least partially surrounds or encompasses the stent in the holding device.

3. The apparatus according to claim 1, wherein the first chamber for the fluid medium at least partially surrounds or encompasses the second chamber, the second chamber being hermetically sealed or isolated from the first chamber.

4. The apparatus according to claim 3, wherein the first chamber for the fluid medium substantially wholly surrounds or encompasses the second chamber, and wherein the wall defining the second chamber has a substantially tubular or cylindrical form.

5. The apparatus according to claim 1, wherein the machining tool comprises a file or a honing mandrel and being axially insertable into the stent when the stent is held by the holding device.

6. The apparatus according to claim 5, wherein the machining tool is rotatable about an axis of rotation and is insertable into the stent along a direction of the axis of rotation; and/or wherein the machining tool is elongate, and a longitudinal axis of the machining tool extends substantially parallel to a longitudinal axis of the stent.

7. The apparatus according to claim 6, wherein the machining tool is adapted for reciprocating movement relative to the stent held by the holding device; or wherein the holding device is adapted for reciprocating movement relative to the machining tool.

8. The apparatus of claim 7, wherein the apparatus further comprises a carriage for supporting the holding device, the carriage adapted for reciprocating movement relative to the machining tool along the longitudinal axis of the machining tool.

9. A method of processing a medical stent, comprising:
holding a stent with a holding device, the holding device comprising a housing having a first end, a second end, a first chamber filled with a fluid medium, a second chamber located within the first chamber and defining a lumen extending from a first opening in the first end to a second opening in the second end for receiving the stent within the second chamber, and a flexible barrier separating the first chamber from the second chamber, wherein selective pressurization of the fluid medium causes the flexible barrier to contact an exterior surface of the stent and exert a substantially uniform pressure to substantially the entire exterior surface of the stent; and processing the stent with a processing device while holding the stent with the holding device, the processing device including a machining tool for processing the stent held by the holding device, the machining tool extending the entire length of the lumen and beyond both ends of the housing, wherein the step of holding the stent comprises pressurizing the first chamber for the fluid medium to exert pressure around the stent.

10. The method according to claim 9, wherein processing the stent comprises machining the stent with the machining tool, wherein machining the stent includes: applying an abrasive medium to the machining tool, and/or inserting the machining tool axially into the stent when the stent is held by the holding device, and/or rotating the machining tool about an axis of rotation, the axis of rotation being substantially parallel to a central axis of the stent.

11. The method according to claim 9, wherein processing the stent comprises reciprocally moving the stent held by the holding device relative to the machining tool; or wherein machining the stent comprises reciprocally moving the machining tool relative to the stent held by the holding device.

* * * * *